United States Patent [19]

Miller

[11] 4,372,917
[45] Feb. 8, 1983

[54] CONTACT LENS STERILIZING APPARATUS

[75] Inventor: Harold M. Miller, Whitinsville, Mass.

[73] Assignee: American Optical Corporation, Southbridge, Mass.

[21] Appl. No.: 318,299

[22] Filed: Nov. 5, 1981

[51] Int. Cl.³ .......................... A61L 3/00; A61L 13/00
[52] U.S. Cl. ....................................... 422/116; 74/3.5; 74/3.54; 422/117; 422/236; 422/237
[58] Field of Search ............... 422/116, 117, 211, 236, 422/237; 74/3.5, 3.54

[56] References Cited

U.S. PATENT DOCUMENTS

| | | | |
|---|---|---|---|
| D. 242,265 | 11/1976 | Ryder et al. ..................... | D32/1 R |
| 3,912,451 | 10/1975 | Gaglia, Jr. ............................ | 134/42 |
| 4,011,941 | 3/1977 | Parsons ................................ | 206/5.1 |
| 4,013,410 | 3/1977 | Thomas et al. ..................... | 74/3.5 X |
| 4,143,116 | 3/1979 | Meltzer ............................... | 422/116 |

*Primary Examiner*—Arthur D. Kellogg
*Attorney, Agent, or Firm*—Kenway & Jenney

[57] ABSTRACT

A timer controlled container inverting apparatus is constructed and arranged to commence timing out for container inversion only after setting of proper inversion time and reception of the container in the apparatus e.g. a vial containing a contact lens in sterilizing solution and oriented for sterilizing process commences process timing only upon application of the vial to the timing apparatus. Shortening of proper sterilizing time is prevented and inversion is effected rapidly at completion of the sterilizing process.

6 Claims, 9 Drawing Figures

CONTACT LENS STERILIZING APPARATUS

BACKGROUND OF THE INVENTION

1. Field of the Invention

The present invention relates to improvements in timer controlled container inverting apparatuses more particularly of the type used to control duration of contact lens sterilization.

2. Discussion of the Prior Art

Among the various well-known techniques of sterilizing articles such as contact lenses is that of immersion in hydrogen peroxide followed by neutralization or decay thereof for avoidance of eye irritation. Those interested in details of such a sterilization system may refer to U.S. Pat. No. 3,912,451. Additionally, U.S. Pat. Nos. 4,143,116 and 4,013,410 exemplify prior art apparatuses which are useful in carrying out timed chemical solution sterilization and automatic solution neutralization by lens container inversion. These devices, however, fail to offer a needed protection against accidental or otherwise occurring inadequate sterilization process. Intentional or negligent partial winding of prior art timing devices or allowing the devices to run after winding without vial loading wastes sterilizing time. Improperly wound container inverting devices and/or late loading of sterilizing containers leads to premature inversion and solution neutralization with a consequence of possible inadequate lens sterilization and the chance of eye contamination with reuse of the lens.

Accordingly, it is an object of the present invention to provide improvements in container inverting apparatuses for sterilizing small articles such as contact lenses.

More particularly, an object of the invention is to avoid the heretofore possibility of inadvertently or otherwise shortening proper lens sterilizing cycles in timed container inverting apparatuses.

Still another object is to provide positive and rapid container inversion at the end of each timed sterilizing cycle for immediate initiation of neutralization of sterilizing chemicals.

Other objects and advantages of the invention will become apparent from the following description.

SUMMARY OF THE INVENTION

The foregoing objectives and their corollaries are accomplished with a timer-controlled container inversion apparatus designed to require setting, e.g. winding, to predetermined full sterilizing cycle time before commencement of timing out and more particularly requiring application of the container to the apparatus for initiation of its timing out operation. Rapid and positive container inversion is provided at completion of timing out, the apparatus thereafter being inoperable for article sterilization purposes without resetting to full cycle timing position.

Details of the invention will become readily apparent from the following description when taken in conjunction with the accompanying drawings in which.

Figure 3:
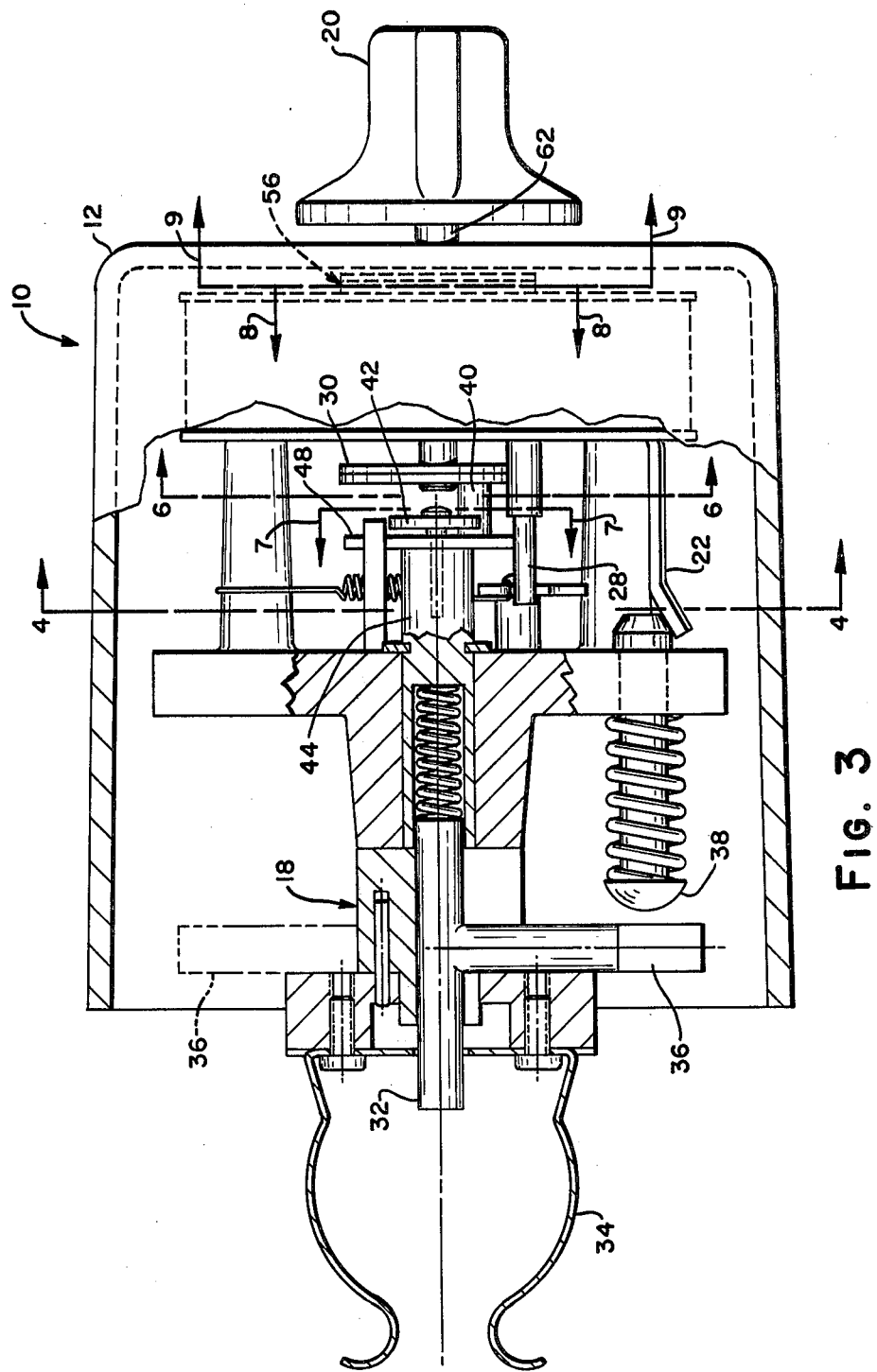
FIG. 3 is an enlarged plan view of the apparatus of FIGS. 1 and 2 with portions broken away for convenience of illustration of internal components thereof.
Figures 8, 9:
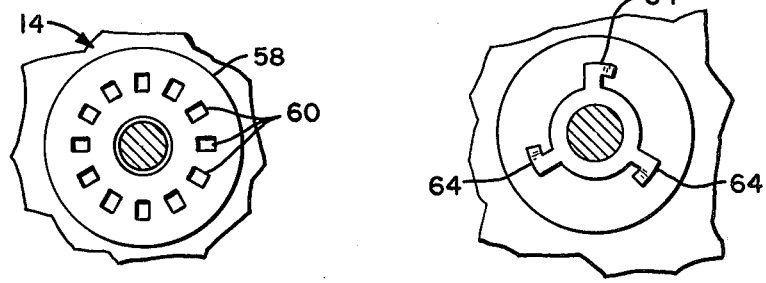

FIGS. 8 and 9 are taken along lines 8—8 and 9—9 of FIG. 3 looking in the directions of respective arrows.

DESCRIPTION OF THE PREFERRED EMBODIMENTS

Referring to the drawings, sterilizing apparatus 10 supported by housing 12 comprises a spring driven timing mechanism hereinafter referred to as timer 14 and a container 16 supporting and inverting mechanism hereinafter referred to as flipper 18.

Spring driven timer 14 is, per se, of conventional construction with time setting knob 20 used to wind its driving spring (not shown). Knob 20 presets, with maximum allowed rotation, a given timing cycle (e.g. two hours). Other timing cycles may, of course, be provided for in conventional fashion.

Figure 6:
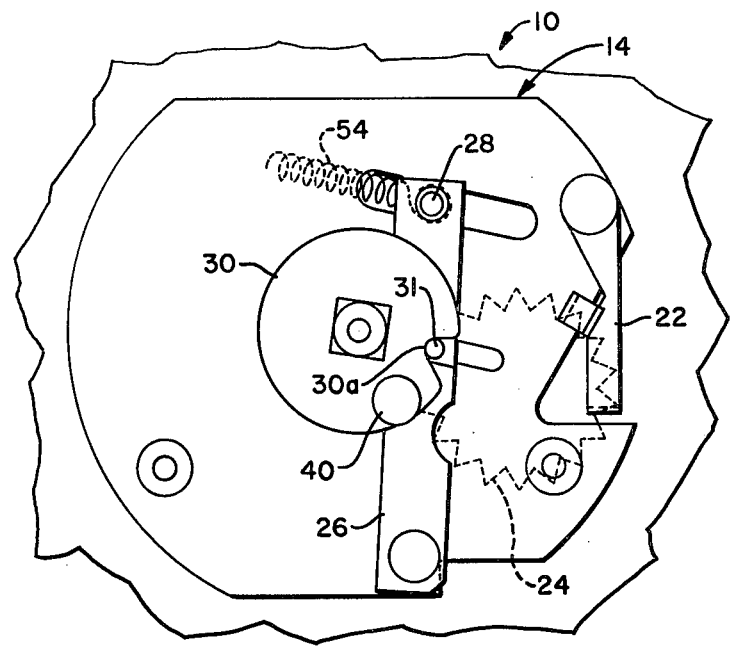
FIG. 6 is a view of internal components of the present apparatus taken generally along lines 6—6 of FIG. 3 looking in the direction of the arrows.
Figure 7:
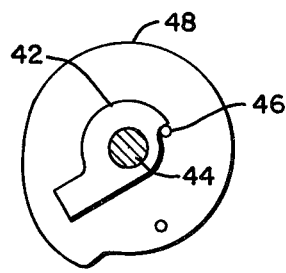
FIG. 7 is a view of other apparatus components taken approximately along line 7—7 of FIG. 3 looking in the direction of the arrows.

Escapement locking lever 22 normally locks timer 14 against timing out, e.g. when in a position against escapement wheel 24 as shown in FIG. 6.

Trip lever 26, having actuating arm 28, is set for timed actuation by cam 30 which is rotatable with knob 20. Low point 30a receives follower pin 31 on lever 26 at the end of a timing cycle (FIG. 6) and remaining edges of cam 30 function to set trip lever 26 to the position shown in FIG. 4. This setting of trip lever 26 is accomplished simultaneously with spring winding of timer 14.

Figure 4:
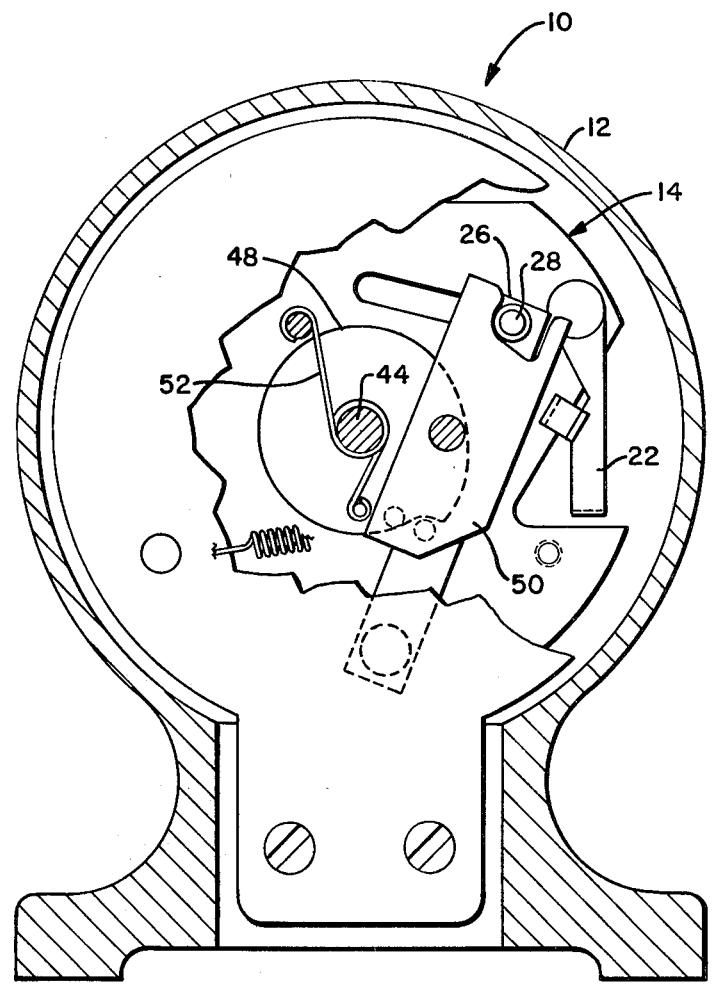
FIG. 4 is a cross-sectional view taken approximately along line 4—4 of FIG. 3.

Timer 14, to the extent thus far described, is of conventional design and commercially available, e.g. from M. H. Rhodes, Inc. of Avon, Conn., USA. A Rhodes, Inc. product identified as Mark-Time 1900 is available in the form described above. It should be understood, however, that timer 14 may be electrically operated, e.g. with dry cells and motor replacing the above-mentioned driving spring and actuable only upon setting of lever 26 as shown in FIG. 4 with knob 20.

Flipper 18 which is also preset with knob 20 for time-delayed inversion in a manner to be described shortly, is triggered for such inversion by actuating arm 28 at completion of timer 14 run out.

Figure 1:
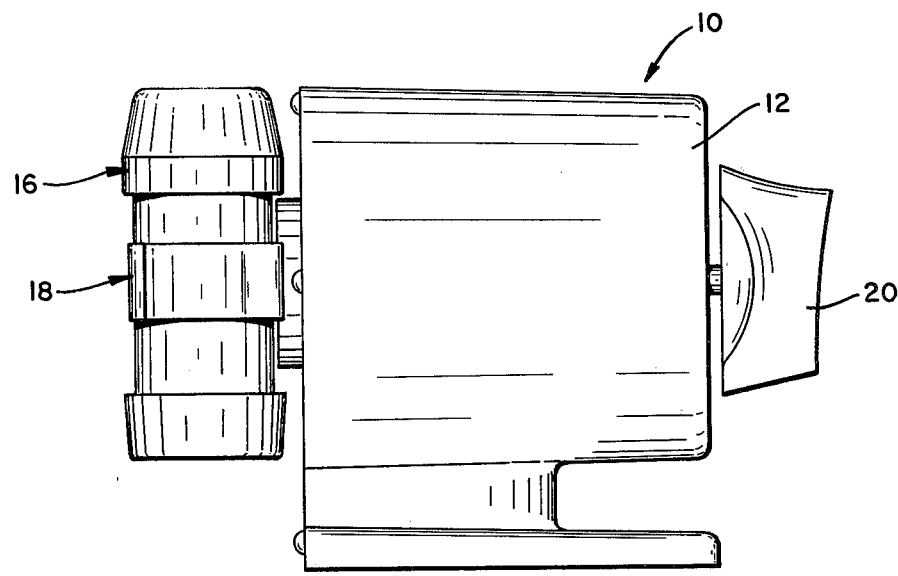
FIG. 1 is a side elevational view of a preferred embodiment of the invention.
Figure 2:
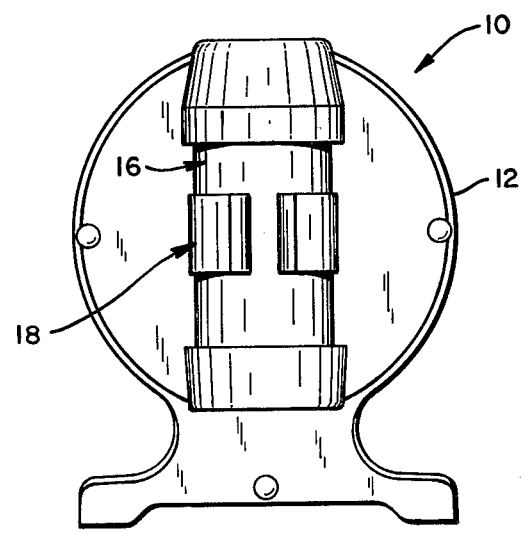
FIG. 2 is a rear view of the apparatus of FIG. 1.

Initiating timing out of a preset knob wound cycle is release of escapement wheel 24 by outward swinging of escapement locking lever 22. To this end, flipper 18 is provided with trip pin 32 spring biased into spring clamp 34 which receives a sterilizing vial or other such container as shown in FIGS. 1 and 2. Trip pin 32, in turn, has lateral arm 36 adapted to engage push rod 38 located intermediately of escapement lever 22 and arm 36. Push rod 38, being spring biased toward arm 36, functions to pivot escapement lever 22 away from escapement wheel 24 when pushed against lever 22. By insertion of a vial or similar article into clamp 34, arm 36 of pin 32 is forced against push rod 38 and push rod 38, in turn, against lever 22. This starts the timer.

The above operation takes place only with flipper 18 finally rotated to the position illustrated in FIG. 3, i.e. from a previously 180° out of the way position where arm 36 extends as shown with broken lines in FIG. 3.

Setting flipper 18 to the position of full line illustration in FIG. 3 is accomplished with rotation of knob 20 which, as mentioned above, winds timer 14 and cocks trip lever 26 to the position shown in FIG. 4.

During the winding of knob 20 and cam 30 which cocks lever 26, dog 40 on cam 30 (FIGS. 3 and 6), engages dog cam 42 on flipper shaft 44 which, in turn, engages pin 46 on flipper cam 48 bringing flipper cam 48 to a cocked position against lever 50, i.e. lever 50 is brought to the cocking position (FIG. 4) by operation of trip lever arm 28.

Figure 5:
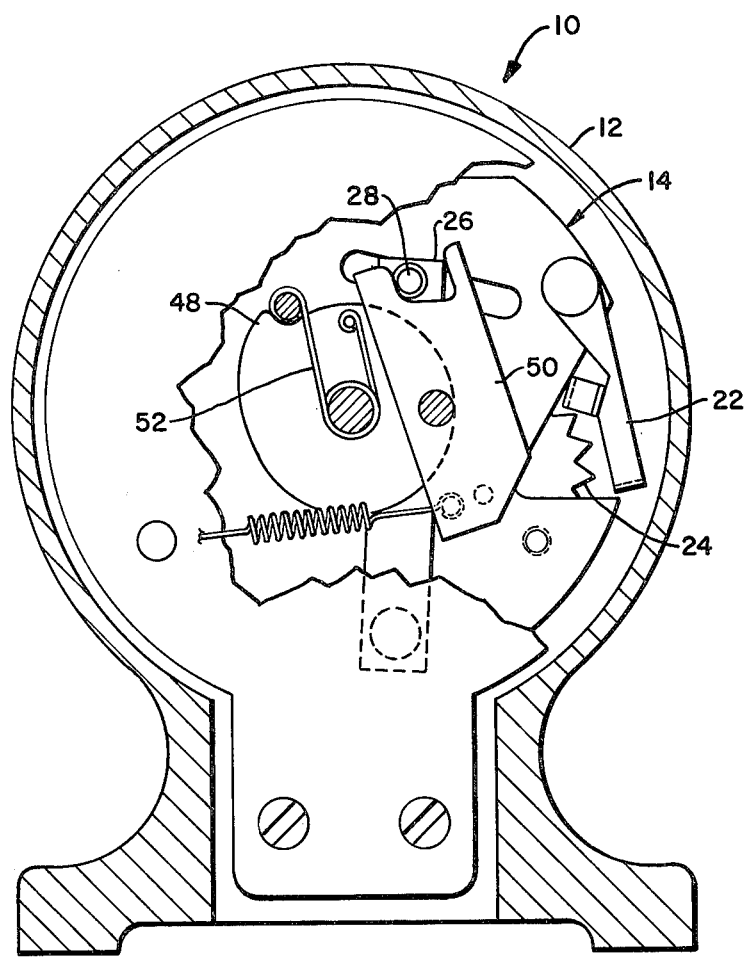
FIG. 5 is a view of the apparatus also taken along line 4—4 of FIG. 3 but illustrating various components thereof in a different operative relationship according to function of the apparatus to be described hereinafter.

At the same time, flipper torsion spring 52 FIGS. 4 and 5) becomes stressed for immediate flipping (inversion) of flipper 18 upon release of cam 48 by movement of cocking lever 50 at end of timer 14 timing cycle as will now be described.

In the course of timer 14 timing out from full winding position (FIG. 4), cam 30 (FIG. 6) finally returns to the illustrated position of accepting follower pin 31 at low point 30a. This, in turn, causes trip lever 26 to swing back under the tension of spring 54 shown in FIG. 6. In so doing, lever 50 releases flipper cam 48 allowing torsion spring 52 to rapidly rotate flipper 18 through 180° and invert container 16 held in spring clamp 34. The above timing out procedure provides a sterilization cycle, e.g. for contact lenses placed in a vial 16 containing hydrogen peroxide and inversion of the vial by flipper 18 at completion of the said timing out causes decay or neutralization of the hydrogen peroxide for non-irritating reuse of lenses so sterilized. Catalysts contacted by the sterilizing solution only upon vial inversion initiate the neutralization process.

Details of useful vial and catalyst constructions may be had by reference to U.S. Pat. Nos. 3,912,451; 4,013,410; 4,011,941; and Des. 242,265.

Further featured in the present apparatus is a one direction winding clutch generally indicated by reference numeral 56 in FIG. 3. This clutch prevents manual reversing of winding knob 20, i.e. winding can only continue in one direction. Partial unwinding, i.e. shortening of predetermined sterilizing cycle, is prevented.

While various forms of single direction clutches may be used, one such apparatus is depicted in FIGS. 8 and 9 for purposes of illustration only. In this connection, one clutch component comprises plate 58 having perforations 60 and a second clutch component comprises a number of laterally extended spring fingers 64 designed to ride over perforations 60 in one direction and drop thereinto when oppositely rotated to prevent such opposite rotation. It should be understood that the components of FIGS. 8 and 9 are normally positioned in face-to-face relationship as indicated by broken lines in FIG. 3.

From the foregoing, it can be seen that the present apparatus prevents less than full winding of a sterilizing cycle time and cannot be turned back for shortening of cycle time after full winding. Timing out cannot be initiated without reception of a sterilizing vial or similar container, removal of the container during timing out stops the timing cycle, rapid and full 180° container inversion takes place at completion of the sterilizing cycle and restarting the apparatus requires repeat of full procedure of full cycle winding and container application for start up.

It is intended that the foregoing disclosure and accompanying illustrations be exemplary of the invention and not delimiting of its scope. All modifications of process or equipment apparent to those skilled in the art are considered to be within the scope of this invention.

I claim:

1. In container inverting apparatus having a timer operated trip lever associated with container supporting and inverting means and a timer escapement locking lever for controlling apparatus timing out, said container supporting and inverting means comprising:
   an axially rotatable flipper mechanism;
   spring means biasing said flipper mechanism in one axially rotatable direction to a stop position;
   means for approximately 180° oppositely rotatably setting said flipper mechanism against the bias of said spring,
   means for cocking said flipper mechanism at said approximately 180° setting, said timer trip lever being associated with said cocking means for releasing said flipper member at end of timing out of said timer and permitting spring initiated return rotation to said stop position;
   a container receiving clip on said flipper mechanism including therewithin means for initiating timing out of said timer by reception of said container, said 180° return rotation of said flipper for container inversion being effected at end of said timing out.

2. Container inverting apparatus according to claim 1 wherein said means for initiating said timing out of said timer includes a sliding trip pin intended for engagement and depression into said clip by placement of a container therein, there being lateral means on said trip pin for actuating said timer escapement locking lever upon depression of said pin into said container clip.

3. Container inverting apparatus according to claim 2 wherein said flipper mechanism sliding trip pin is spring biased into said container clip and said lateral means for actuating said timer escapement locking lever includes an arm and spring loaded push rod means between said arm and escapement locking lever, said rod being urged against said lever by said arm with depression of said trip pin into said clip for initiating timing out of said apparatus.

4. Container inverting apparatus according to claim 2 wherein a container received in said flipper mechanism is oriented vertically when said flipper mechanism is disposed at said approximately 180° setting and is inverted to a second vertical orientation with said flipper mechanism at said stop position.

5. Container inverting apparatus according to claim 2 wherein said means for setting said flipper mechanism against the bias of said spring includes a winding knob on said timer and said flipper mechanism cocking means includes a cam rotatable with said timer winding knob, said timer trip lever riding against said cam.

6. Container inverting apparatus according to claim 5 further including clutch means associated with said timer knob for preventing manual timer unwinding.

* * * * *